United States Patent
Nagarkatti et al.

(10) Patent No.: US 10,167,512 B2
(45) Date of Patent: *Jan. 1, 2019

(54) LEUKOCYTE MICRORNAS FOR USE IN DIAGNOSIS AND TREATMENT OF ENDOMETRIOSIS

(71) Applicant: University of South Carolina, Columbia, SC (US)

(72) Inventors: Mitzi Nagarkatti, Columbia, SC (US); Juhua Zhou, Lexington, SC (US); Bruce A. Lessey, Greenville, SC (US); Prakash Nagarkatti, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/592,428

(22) Filed: May 11, 2017

(65) Prior Publication Data

US 2017/0247763 A1 Aug. 31, 2017

Related U.S. Application Data

(63) Continuation of application No. 14/662,574, filed on Mar. 19, 2015, now Pat. No. 9,650,676.

(60) Provisional application No. 61/955,519, filed on Mar. 19, 2014.

(51) Int. Cl.
*A61K 31/60* (2006.01)
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

PUBLICATIONS

Wang et al (J Clin Endocrinol Metab 98:281-289, 2013—Supplemental Table 1 only) (Year: 2013).*
Feng, et al., "Decreased plasma cytokines are associated with low platelet counts in aplastic anemia and immune thrombocytopenic purpura," *J Thromb Haemost* (2012) 10(8); pp. 1616-1623.
Hawkins, et al. "Functional microRNA involved in endometriosis," *Mol Endocrinol* (2011) 25(5): pp. 821-832.
Hey-Cunningham, et al., "Endometrial stromal cells and immune cell populations within lymph nodes in a nonhuman primate model of endometriosis," *Reprod Sci* (2011) 18(8) pp. 747-754.
Hou, et al. "Cytokine array analysis of peritoneal fluid between women with endometriosis of different stages and those without endometriosis." *Biomarkers* (2009) 14(8) pp. 604-618.
Hu, et al., "Association of Serum Cytokines, Human Growth Hormone, Insulin-Like Growth Factor (IGF)-I, IGF-II and IGF-Binding Protein (IGFBP)-3 with Coronary Artery Disease," *Chin J Physio* (2012)155(4) pp. 267-273.
Malumbres, et al. "Expression of miRNAs in lymphocytes: a review," *Methods Mol Biol* (2010) 667 pp. 129-143.
O'Connell, et al., "MicroRNA-155 promotes autimmune inflammation by enhancing inflammatory T cell development." *Immunity* 33(4) pp. 607-619.
Rier, et al.; "Immune aspects of endometriosis: relevance ofthe uterine mucosal immune system." *Semin Reprod Endocrinol.* (1997) 15(3): 209-220.
Rodriguez, et al., "Requirement of bic/microRNA-155 for normal immune function." *Science* (2007) 316(5824) pp. 608-611.
St Georgiev, et al., "Cytokines and their role as growth factors and in regulation of immune responses." *Ann NY Acad Sci* (1993) 685 pp. 584-602.
Steppich, et al.;"Cytokine profiles and T cell function in acute coronary syndromes." *Atherosclerosis* (2007) 190(2) pp. 443-451.
Wang, et al.; "Circulating MicroRNAs Identified in a Genome-Wide Serum MicroRNAs Identified in a Genome-Wide Serum MicroRNA Expression Analysis as Nonivasive Biomarkes for Endometriosis." *I Clin Endocrinol Metab*, (2013) 98(1) pp. 281-289.
Xiao, et al.,"MicroRNA control in the immune system: basic principles."*Cell*(2009) 136(1) pp. 26-36.
Bryant, et al., "Cytokine-mediated regulation of humab B cell differentiation into Ig-secreting cells: predominant role of IL-21 produced by CXCR5+ T follicular helper cells." *J Immunol* (2007) 179(12); pp. 8180-8190.
Feinburg, et al., "The epigenetic progenitor origin of human cancer." *Nat Rev Genet* (2006) 7(1) pp. 21-33.
Egger, et al., "Epigenetics in human disease and prospects for epigenetic therapy." *Nature* (2004) 429(6990) pp. 457-463.
Du, et al., "MicroRNA miR-326 regulates TH-17 differentiation and is associated with the pathogenesis of multiple sclerosis" *Nat Immunol* (2009) 10(12) pp. 1252-1259.
Anglicheau, et al., "MicroRNAs: small RNAs with big effects." *Transplantation* (2010) 90(2) pp. 105-112.
Ohlsson Teague et al (Molec Endocrinol23:265-275, 2009).
Filigheddu et al (J Biomed Biotech No. I 2010:1-29, 201 0).
Laudanski et al (Reproductive Bioi and Endocrinol 11:78-84, 2013).
Haider et al (PLoS ONE 9(2):1-11, 2014)
Suryawanshi et al (Ciin Cancer Res 19:1213-1224, 2013).
Wang et al (J Clin Endocrinol Metab 98:281-289, 2013).

* cited by examiner

*Primary Examiner* — Craig D Ricci
(74) *Attorney, Agent, or Firm* — Dority & Manning, P.A.

(57) ABSTRACT

Methods for diagnosis and treatment of endometriosis are described. Methods utilize the recognition that leukocyte miRNAs can be dramatically dysregulated subjects suffering from endometriosis. Accordingly, leukocyte miRNAs, as well as polynucleotides encoding the miRNAs, can be utilized in the diagnosis and treatment of endometriosis.

4 Claims, 5 Drawing Sheets

LEUKOCYTE MICRORNAS FOR USE IN DIAGNOSIS AND TREATMENT OF ENDOMETRIOSIS

CROSS REFERENCE TO RELATED APPLICATION

The present application is a Continuation Application of U.S. application Ser. No. 14/662,574 having a filing date of Mar. 19, 2015, which claims filing benefit of U.S. Provisional Patent Application Ser. No. 61/955,519 titled "Leukocyte MicroRNAs as Biomarkers for Endometriosis" of Nagarkatti, et al. filed on Mar. 19, 2014, the disclosures of which are incorporated by reference herein.

GOVERNMENT SUPPORT CLAUSE

This invention was made with government support under P01AT003961 awarded by the National Institutes of Health. The government has certain rights in the invention.

BACKGROUND

Endometriosis is an estrogen-dependent, inflammatory disease affecting approximately 176 million women worldwide. It occurs when cells from the lining of the uterus grow in other areas of the body. It usually leads to pain, irregular bleeding, and infertility.

It has been reported that immune dysregulation may play a role in endometriosis (Rier and Yeaman 1997). For instance, animal modeling studies have indicated that lymph node immune cell populations including T cells, dendritic cells and B cells were increased and endometrial stromal cells were significantly increased in lymph nodes from animals with induced endometriosis (Hey-Cunningham, Fazleabas et al. 2011).

In addition, it has been documented that cytokines may play a critical role in immune cell differentiation, growth and functions (St Georgiev and Albright 1993; Bryant, Ma et al. 2007; Steppich, Moog et al. 2007). Alterations in cytokine expression associated with inflammation have long been observed in individuals with immune-mediated diseases (Feng, Scheinberg et al. 2012; Hu and Hwang 2012). Cytokines may be dysregulated in patients with endometriosis (Hou, Sun et al. 2009), suggesting that cytokines may play a role in endometriosis.

Epigenetic events are crucial in the control of both normal cellular processes and abnormal events associated with cancer (Feinberg, Ohlsson et al. 2006) and other human diseases (Egger, Liang et al. 2004). Major epigenetic mechanisms include DNA methylation, covalent post-translational modifications of histone proteins, and RNA-mediated gene silencing such as via small interfering RNA (siRNA) and microRNA (miRNA). It has been reported that miRNAs, small noncoding RNAs that regulate gene expression by binding to complementary target mRNAs and inhibiting their translation, have been shown to play a crucial role in the regulation of cytokine genes (O'Connell, Kahn et al.; Xiao and Rajewsky 2009), and are involved in the production and functions of immune cells. The specific role of some individual miRNAs has been demonstrated in hematopoiesis and immune cell regulation. For example, miR-223 is involved in human granulopoiesis, erythropoiesis and B cell differentiation (Malumbres and Lassos 2010), miR-155 promotes Th2 cell differentiation (Rodriguez, Vigorito et al. 2007), and miR-326 promotes Th17 cell development (Du, Liu et al. 2009).

miRNAs have also been implicated in immune regulation. For example, miR-146a regulates the immune response to bacterial infections and miR-181a modulates the sensitivity of T lymphocytes to antigens by regulating expression levels of various phosphatases from the T-cell receptor signaling (Anglicheau, Muthukumar et al. 2010).

Recent studies indicate that microRNAs may play a role in endometriosis (Hawkins, Creighton et al. 2011; Wang, Zhao et al. 2013). Elucidation of roles of specific microRNA dysregulated in endometrial patients could have great implications in understanding the pathogenesis of endometriosis and developing diagnostic markers and therapeutic targets for endometriosis.

What are needed in the art are treatment methods for endometriosis that include early detection of the disease state.

SUMMARY

According to one embodiment, a method for diagnosing and treating endometriosis in a subject is disclosed. For instance, a method can include analyzing a test sample to determine a quantity of a leukocyte microRNA in the test sample (i.e., either a mature microRNA or a polynucleotide that encodes the mature leukocyte microRNA). The method can also include comparing the quantity of the microRNA in the test sample to a control quantity of the leukocyte microRNA. More specifically, a determination that the quantity of the leukocyte microRNA in the test sample differs from the control quantity by a factor of about 2 or greater can be indicative of endometriosis in the subject. The method can further include administering a treatment for endometriosis to the subject.

According to another embodiment, a method for diagnosing and treating endometriosis is disclosed. For instance, a method can include analyzing a test sample for the overexpression in the subject of one or more cytokines selected from IL-17, IFN-α, IL-4, and IL-10 by determining in the sample the quantity of a leukocyte microRNA, the leukocyte microRNAs being microRNA-150a, microRNA-146a, microRNA-505, microRNA-320a, and let-7a microRNA precursor or combinations thereof. The method can also include comparing the quantity of the microRNA in the test sample to a control quantity of the leukocyte microRNA. More specifically, a determination that the quantity of the leukocyte microRNA in the test sample differs from the control quantity by a factor of 2 or greater can be indicative of endometriosis in the subject. The method can further include administering a treatment for endometriosis to the subject.

DETAILED DESCRIPTION

The following description and other modifications and variations to the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the following description is by way of example only, and is not intended to limit the invention.

The present disclosure is generally directed to the diagnosis and treatment of endometriosis. More specifically, the present disclosure is directed to recognition that the dysregulation of leukocyte microRNAs is indicative of endometriosis, and that this recognition can be utilized in the diagnosis and/or treatment of endometriosis. For example, in one embodiment, determination of the upregulation (overexpression) or downregulation (underexpression) of leukocyte microRNAs can be utilized in a protocol for treatment of endometriosis. In another embodiment, determination of the upregulation or downregulation of certain leukocyte microRNAs can be utilized to determine the overexpression of certain inflammatory cytokines, which can be utilized in diagnosis and/or treatment of endometriosis.

According to the present disclosure, it has been determined that leukocyte miRNAs can be dramatically dysregulated in test samples of subjects suffering from endometriosis. For example, leukocyte miRNAs can be dramatically dysregulated in the peripheral blood mononuclear cells in subjects suffering from endometriosis. Accordingly, determination of the level in a test sample of mature leukocyte miRNAs and/or polynucleotides encoding the mature miRNAs, can be utilized in the diagnosis and treatment of endometriosis. Techniques for miRNA expression analysis in test samples are known in the art and reliable and as such the disclosed methods have a great potential in clinical diagnosis and treatment for endometrial patients.

As used herein, the term "test sample" generally refers to a biological material suspected of containing a microRNA of interest or a polynucleotide encoding a microRNA of interest. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. In addition, a solid material suspected of containing a microRNA or a polynucleotide encoding the microRNA may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the microRNA.

In addition, it should be understood that any polynucleotide encoding a microRNA is encompassed herein including genes encoding microRNA (e.g., MIR-xxx, in which xxx is the numerical reference to the particular microRNA), primary microRNA transcripts (pri-mRNA, e.g., mir-xxx), precursor microRNA transcripts (pre-mRNA, e.g., mir-xxx), as well as mature microRNA (mRNA; e.g., miR-xxx). As used herein, the term "gene" generally refers to a locatable region of a genomic sequence that is involved in producing a microRNA, and includes regulatory regions, introns, transcribed regions and/or other functional sequence regions.

In determination that leukocyte miRNAs may be used as diagnostic markers and therapeutic targets for endometriosis, a number of peripheral blood, peritoneal fluid and endometrial tissues samples from patients diagnosed with endometriosis have been examined. The data demonstrate that leukocyte miRNAs may be used as diagnostic markers, for instance in treatment protocols, and also as therapeutic targets for endometriosis.

Figure 1:
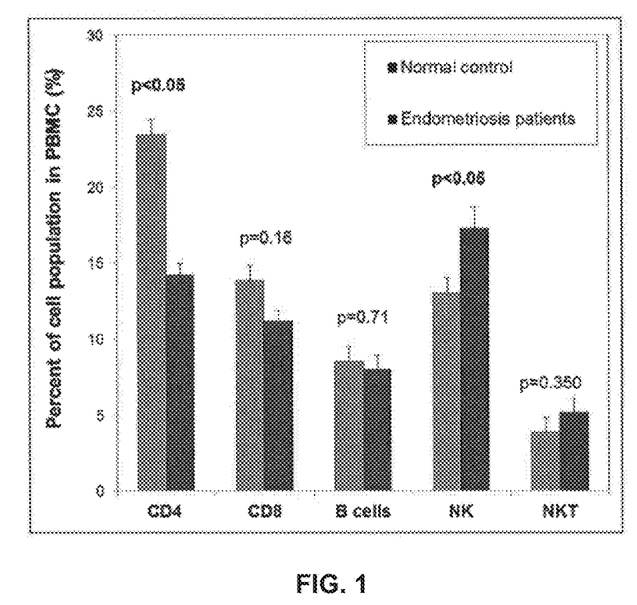
FIG. 1 presents the change in immune cell populations in peripheral blood mononuclear cell (PBMC) samples from endometrial patients as compared with controls.
Figure 2A:
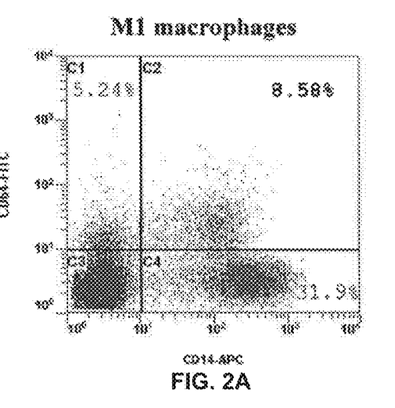
FIG. 2A presents data concerning M1 macrophages in peritoneal buffy coat samples from endometriosis patients.
Figure 2B:
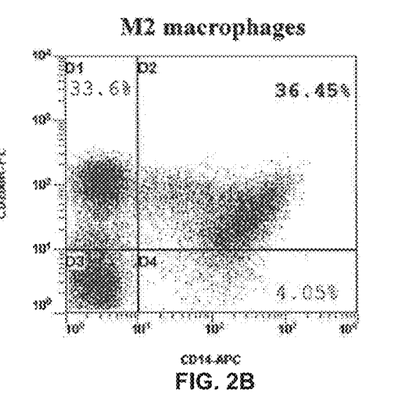
FIG. 2B presents data concerning M2 macrophages in peritoneal buffy coat samples from endometriosis patients.

Flow cytometry has been used to analyze changes in immune cells in the peripheral blood mononuclear cell (PBMC) populations from patients with endometriosis. Analysis demonstrated that CD4+ T cells in the PBMC were significantly decreased in endometriosis patients compared to controls (FIG. 1). However, natural killer (NK) cells were dramatically increased in endometriosis cases compared with normal donors (FIG. 1). In buffy coat samples from peritoneal fluid of endometriosis patients, there were significantly higher levels of CD14+ macrophages, especially M2 macrophages (FIG. 2A; FIG. 2B). These results suggested that immune dysregulation in the patients with endometriosis may play an important role in endometriosis development.

Figure 3:
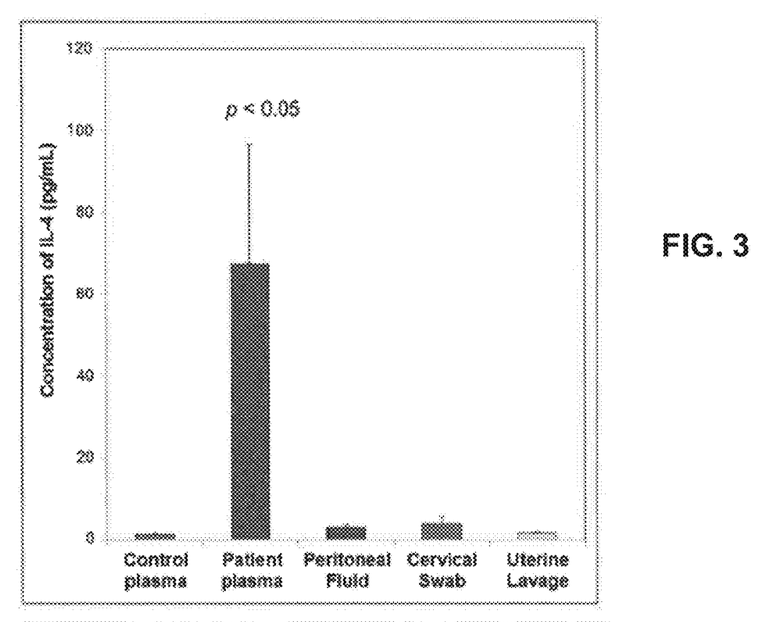
FIG. 3 graphically illustrates increased plasma level of IL-4 in endometrial patients as compared with control subjects and cytokine levels in peritoneal fluid, cervical swab and uterine lavage samples from endometrial patients.
Figure 4:
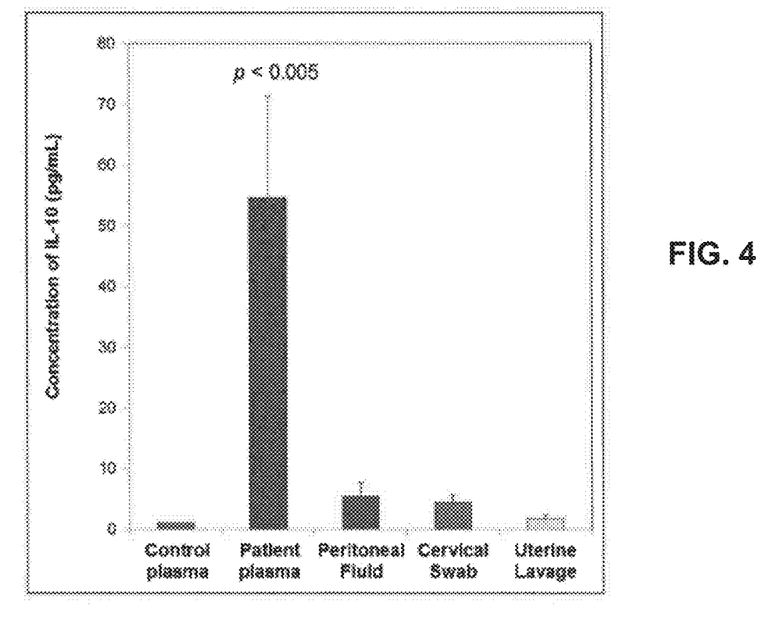
FIG. 4 graphically illustrates increased plasma level of IL-10 in endometrial patients as compared with control subjects and cytokine levels in peritoneal fluid, cervical swab and uterine lavage samples from endometrial patients.
Figure 5:
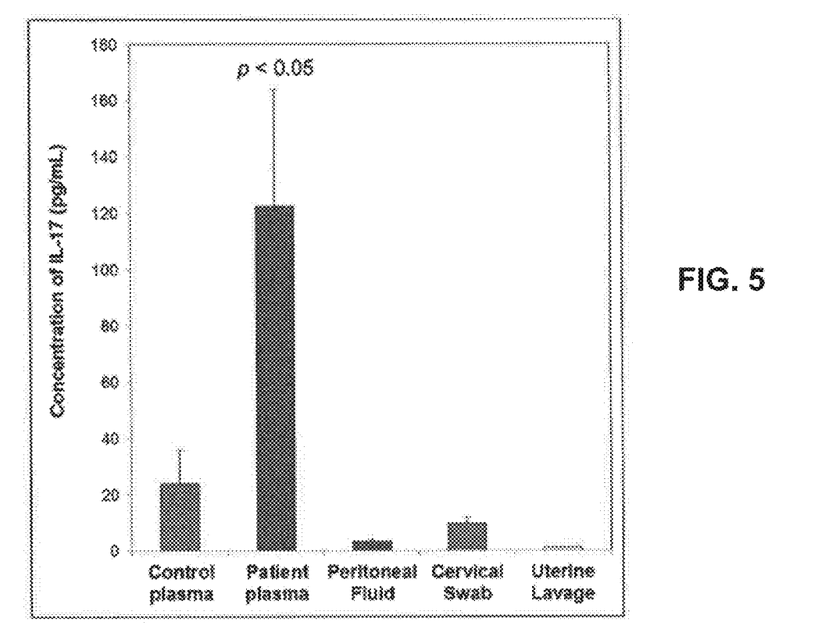
FIG. 5 graphically illustrates increased plasma level of IL-17 in endometrial patients as compared with control subjects and cytokine levels in peritoneal fluid, cervical swab and uterine lavage samples from endometrial patients.
Figure 6:
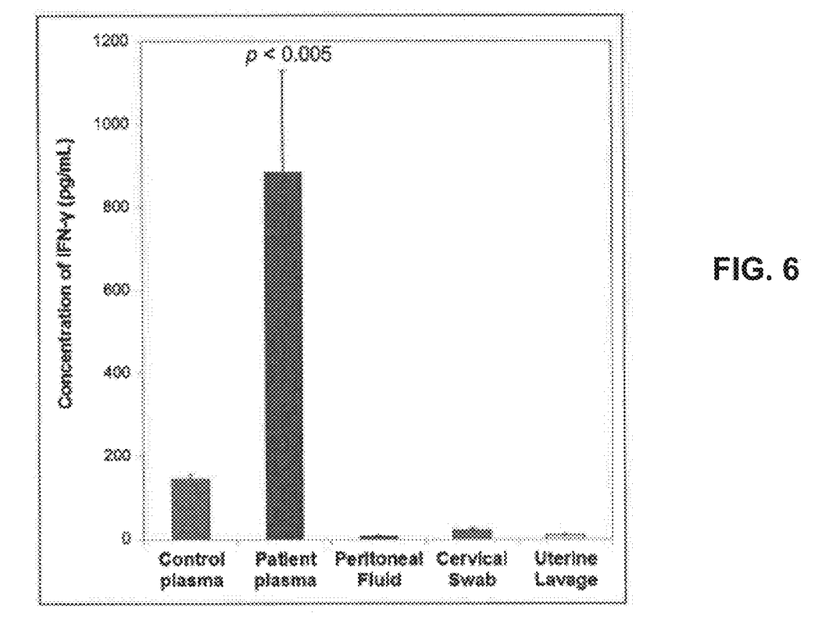
FIG. 6 graphically illustrates increased plasma level of IFN-γ in endometrial patients as compared with control subjects and cytokine levels in peritoneal fluid, cervical swab and uterine lavage samples from endometrial patients.
Figure 7:
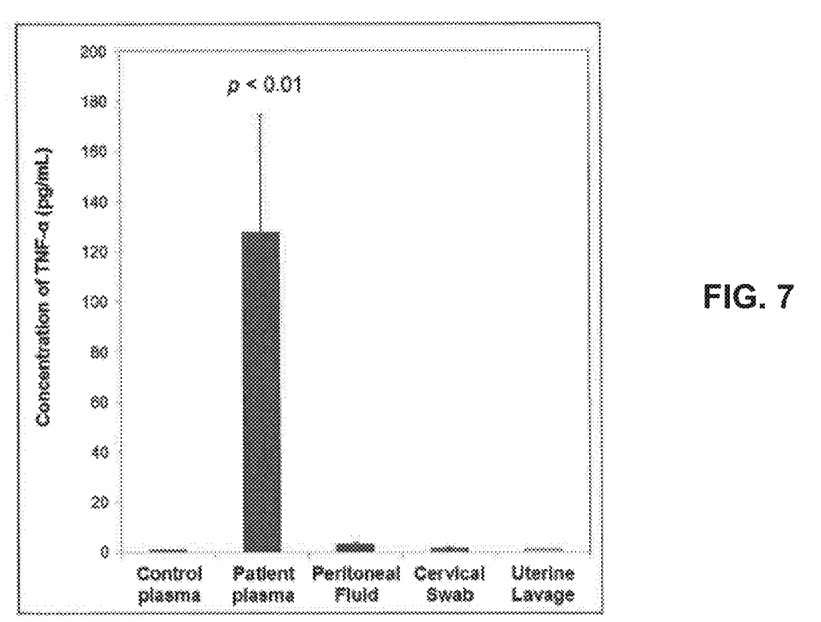
FIG. 7 graphically illustrates increased plasma level of TNF-α in endometrial patients as compared with control subjects and cytokine levels in peritoneal fluid, cervical swab and uterine lavage samples from endometrial patients.

Cytokines mediate and control immune and inflammatory responses. Common human diseases such as allergies, autoimmune diseases, chronic infections, cancer and sepsis are characterized by a dysregulation in the pro-versus anti-inflammatory cytokine balance. Cytokine analysis indicates that anti-inflammatory cytokines such as IL-4 (FIG. 3) and IL-10 (FIG. 4) as well as pro-inflammatory cytokines including IL-17 (FIG. 5), IFN-γ (FIG. 6) and TNF-α (FIG. 7) are significantly increased in the plasma of endometriosis subjects, suggesting that specific cytokines play a role in endometriosis pathogenesis.

Based on in silico studies, it has been determined that both miR-150 and miR-146a can lead to suppressed IL-17 production, miR-505 can inhibit IFN-γ gene expression, miR-320a can inhibit IL-4 and let-7e can inhibit IL-10. In addition, in accord with the present disclosure, it has been determined that these miRNAs (miR-150, miR-146a, miR-320a, miR-505 and let-7e) can be dramatically down-regulated in women with endometriosis. Thus, in endometriosis patients, the decreased expression of these miRNAs may be responsible for the increased expression of these pro- and anti-inflammatory cytokines and this immune dysregulation may be useful in detection and treatment of the pathophysiology in endometriosis.

According to one embodiment, detection of the down-regulation of one or more of the microRNAs microRNA-146a, microRNA-505, microRNA-150, microRNA-320a, and let-7e can be indicative of the over expression of the related cytokines IL-17, IFN-γ, IL4, and IL-10 and thus diagnosis and treatment of endometriosis.

Determination of the down-regulation of the microRNAs can be carried out according to any suitable detection scheme. In general, determination can include assessment of the concentration of the microRNAs in a test sample and comparison of that concentration with a normal control value. As used herein, the term "normal" with regard to concentration of a compound in a test sample generally refers to the average concentration of the compound in a number individuals not affected by endometriosis. For example, the average concentration of the compound in about 10 or more individuals not affected by endometriosis.

Hybridization-based methods for determining the concentration of the targeted miRNA can be used. Hybridization-based methods are direct assay methods that do not necessarily require the amplification of RNA samples. Hybridization-based methods can include, without limitation, Northern blot, microarray, and bead-based flow cytometry. The basic principle of these technologies is to hybridize probes with microRNA contained in the sample and then perform the signal detection.

As used herein, the term "probe" generally refers to any molecule that is capable of binding to a specifically intended target molecule, e.g., a mature microRNA. Probes can be either synthesized or derived from natural materials. Examples of molecules that can be utilized as probes include, but are not limited to, RNA, DNA, proteins, antibodies, and organic monomers.

As is known in the art, "hybridization" methods involve the annealing of a complementary sequence to a target nucleic acid sequence (the sequence to be analyzed). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Hybridization encompasses, but is not limited to, slot, dot and blot hybridization techniques.

Quantitative real-time PCR (qRT-PCR) can also be utilized to determine the concentration of miRNA in the sample. By way of example, one of two qRT-PCR methods for miRNA expression analysis can be used: the poly(A) method (Shi, R. (2005) Biotechnique, 39, 519-525) or the stem-loop method (Chen, C. (2005) Nucleic Acids Res, 33, 1-9). The poly(A) method uses a poly(A) tail added to the 3' end of each mature miRNA by poly(A) polymerase. The tailed miRNAs are then subjected to reverse transcription (RT) using a universal RT primer containing 2 to 3 degenerate nucleotides at 3' end followed by an oligo(dT) and universal reverse primer sequence. The synthesized cDNA is amplified with specific forward and universal reverse primers. This method provides a simple and cost-effective method for miRNA assay.

The stem-loop method uses a designed stem-loop RT primer that contains six specific bases at its 3' end that are complementary to the 3' end of the specific mature miRNA for reverse transcription. The primer for reverse transcription has a stem-loop at its 5' end, which enhances the affinity of miRNA/DNA and avoids annealing of primer and pri- or pre-miRNA.

As utilized herein, the term "primer" refers to an oligonucleotide which is capable of acting as a point of initiation of synthesis when placed under conditions in which primer extension is initiated. An oligonucleotide "primer" can occur naturally, as in a purified restriction digest or be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

Optionally, a detection scheme can include concentrating or isolating the miRNA from a sample. For instance, a method can utilize commercially available anion exchange materials to isolate the microRNA of a sample. Either strong or weak anion exchangers may be employed. By utilizing selected solutions for adsorption and elution, the miRNA of a sample can be purified, concentrated, and substantially isolated.

By employing a solution at known ionic strength for the initial binding of the miRNA to the anion exchange column materials, most of the water soluble components including other electronegative molecules such as proteins (weakly-bound contaminants) can be washed through the column. For elution, the required ionic strength is reached by using known concentrations of a salt such as NaCl, which may be mixed with a buffer to control pH, ideally corresponding to the lowest ionic strength at which the microRNAs will completely elute. Contaminating substances bound to the anion exchange resin with higher stringency than the nucleic acids can thus be retained within the column.

A weak exchanger is one in which primary, secondary, or tertiary amine groups (i.e., protonatable amines) provide exchange sites. The strong base anion exchanger has quaternary ammonium groups (i.e., not protonatable and always positively charged) as exchange sites. Both exchangers can be selected in relation to their respective absorption and elution ionic strengths and/or pH for the miRNA being separated. The solution strengths are higher than the binding strengths.

According to one embodiment, analysis of a sample can be carried out as follows:
  Step 1: Obtain a sample (e.g., a peripheral blood sample) from a subject.
  Step 2: Isolate immune cells (e.g., peripheral blood mononuclear cells) from the sample.
  Step 3: Purify total RNA samples (including miRNAs) from the immune cells.
  Step 4: Perform miScript reverse transcription to convert total RNA into cDNA.
  Step 5: Carry out quantitative real-time PCR using specific miScript primer assay to determine expression level of specific miRNA in the sample.

Step 6: Compare the expression level of the targeted miRNA in the subject with normal control valued.

Step 7: Depending upon the comparison, diagnose the subject with and/or treat the subject for endometriosis.

Disclosed methods are not limited to the down-regulated microRNA mentioned above. For instance, studies have also demonstrated that microRNA-1225-5p, microRNA-572, microRNA-219-1-3p, microRNA-675 and microRNA-886-5p can be significantly up-regulated in subjects diagnosed with endometriosis. Accordingly, in one embodiment, disclosed methods for treatment of endometriosis can include determining the expression level of one or more of microRNA-1225-5p, microRNA-572, microRNA-219-1-3p, microRNA-675 and microRNA-886-5p, optionally in conjunction with one or more of the down-regulated microRNA discussed above, e.g., microRNA-150, microRNA-146a, microRNA-320a, microRNA-505 and let-7e.

Disclosed methods are not limited to the microRNAs mentioned above. Rather, endometriosis treatment methods disclosed herein are directed to leukocyte microRNAs that are up-regulated or down-regulated such that the quantity of the leukocyte miRNA (or the polynucleotide that encodes the leukocyte miRNA) in a test sample differs from that of a control quantity by a factor of 2 or greater, or higher in other embodiments, for instance by a factor of 3 or greater, a factor of 4 or greater, or a factor of 5 or greater in some embodiments.

Figure 8:
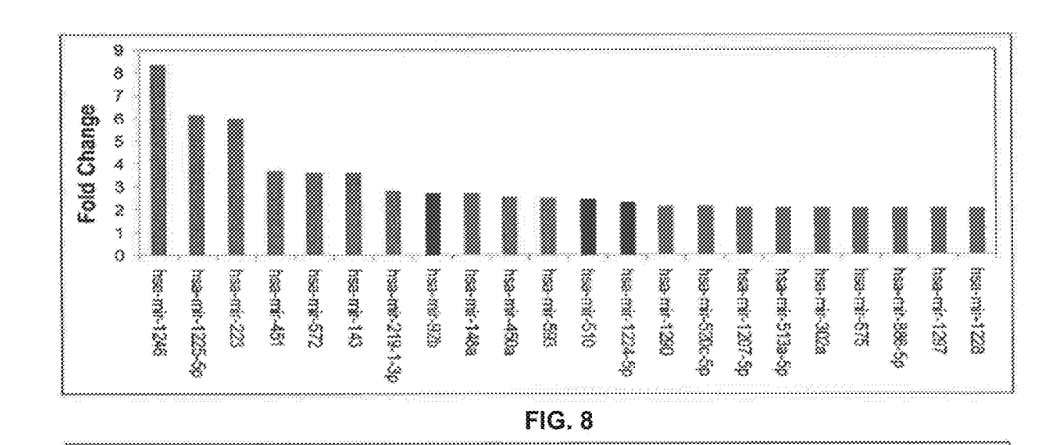
FIG. 8 presents miRNAs exhibiting up-regulation in PBMC from endometrial patients as compared to controls.
Figure 9:
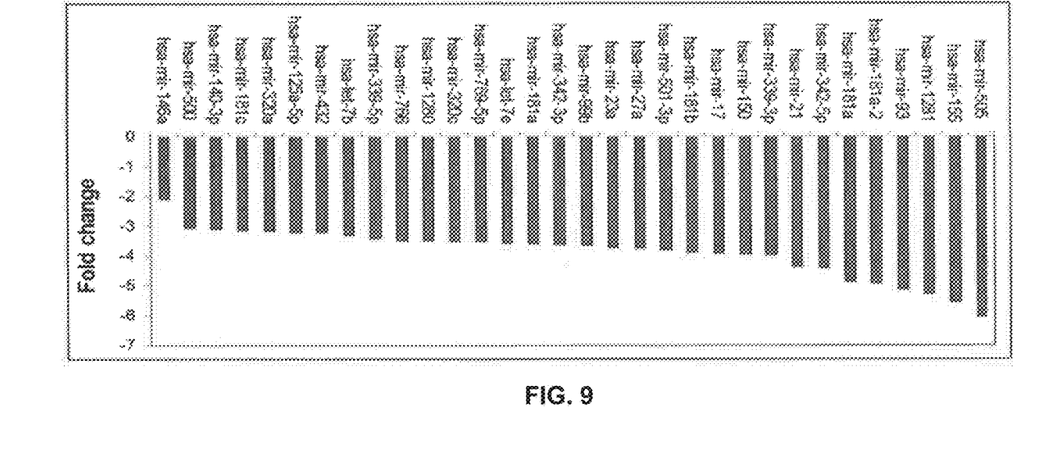
FIG. 9 presents miRNAs exhibiting down-regulation in PBMC from endometrial patients as compared with normal controls.

Examples of leukocyte microRNAs that have been determined to be significantly (i.e., by a factor of 2 or greater) up-regulated or down-regulated in subjects suffering from endometriosis as compared to the expression levels for control subjects are provided in FIG. 8 and FIG. 9.

In one embodiment, a method can include determination that the concentration of one or more of the up-regulated microRNAs of FIG. 8 (microRNA-1246, microRNA-1225-5p, microRNA-223, microRNA-451, microRNA-572, microRNA-143, microRNA-219-1-3p, microRNA-92b, microRNA-148a, microRNA-450a, microRNA-593, microRNA-510, microRNA-1224-5p, microRNA-1290, microRNA-520c-5p, microRNA-1207-5p, microRNA-513a-5p, microRNA-302a, microRNA-675, microRNA-886-5p, microRNA-1297, microRNA-1228) and/or one or more of the down-regulated microRNAs of FIG. 9 (microRNA-505, microRNA-155, microRNA-1261, microRNA-93, microRNA-181a-2, microRNA-181a, microRNA-342-5p, microRNA-21, microRNA-339-3p, microRNA-150, microRNA-17, microRNA-181b, microRNA-501-3p, microRNA-27a, microRNA-23a, microRNA-99b, microRNA-342-3p, microRNA-181a, let-7e, microRNA-769-5p, microRNA-320c, microRNA-1260, microRNA-766, microRNA-339-5c, microRNA-let-7b, microRNA-432, microRNA-125a-5p, microRNA-320a, microRNA-181c, microRNA-140-3p, microRNA-500, microRNA-146a) differs from that of a control quantity by a factor of 2 or greater or higher in other embodiments, for instance by a factor of 3 or greater, a factor of 4 or greater, or a factor of 5 or greater in some embodiments as indicated in FIG. 8 and FIG. 9.

Following determination that the concentration of one or more leukocyte miRNAs in a test sample differs from that of a control concentration by a factor of about 2 or more, a method can also include treating the subject from whom the sample was derived for endometriosis.

The specific treatment utilized for endometriosis can vary depending upon the medical history of the patient, the presence of symptoms and, if so, the nature of the symptoms, the extent of the disease state, and so forth.

Analgesics such as nonsteroidal anti-inflammatory drugs (NSAIDs) can be effective treatment in some cases to relieve pain resulting from endometriosis. Examples of analgesics and/or NSAIDs as may be incorporated in a treatment protocol can include analgesics available over the counter (OTC) at relatively low dosages including acetamide (acetaminophen or paracetamol), acetylsalicylic acid (aspirin), ibuprofen, ketoprofen, naproxen and naproxen sodium, and the like. Prescription analgesics and/or anti-inflammatories as may be incorporated in a treatment protocol may include, without limitation, OTC analgesics at concentrations requiring a prescription, celecoxib, sulindac, oxaprozin, salsalate, piroxicam, indomethacin, etodolac, meloxicam, nabumetone, keteroloc and ketorolac tromethamine, tolmetin, diclofenac, diproqualone, and diflunisal. Narcotic analgesics may include codeine, hydrocodone, oxycodone, fentanyl, and propoxyphene.

A treatment protocol may include one or more steroidal anti-inflammatory compounds, primarily glucocorticoids, including, without limitation, cortisone, dexamethasone, prednisolone, prednisone, hydrocortisone, triamcinolone, and methylprednisolone, betamethasone, and aldosterone.

Hormonal therapies can also be utilized in treatment of endometriosis, often in conjunction with one or more analgesics. Endometrial tissue requires estrogen to grow, and itself produces estrogen. Thus hormonal therapies that lower estrogen levels and/or increase levels of hormones that counteract effects of estrogen can be effective. Oral contraceptives, for example, can reduce or eliminate pain arising from endometriosis. Progestins and androgens (natural or, more commonly, synthetic) can interfere with the monthly cycle of endometrial thickening, breakdown and bleeding. The most widely used progestin, medroxyprogesterone, is typically administered as a depot injection. Androgens, including danazol (17α-ethynyl-17β-hydroxy-4-androsteno[2,3-d]-isoxazole) and gestrinone (ethylnorgestrienone), can be administered orally.

Hormonal therapy can include use of drugs that interact with gonadotropin releasing hormone (GnRH), whether as agonists (e.g., nafarelin or leuprolide) or antagonists, and further can include use of aromatase inhibitors that block conversion of androgens such as androstenedione and testosterone to estrogen.

Hormonal therapies can be administered systemically, for example orally, intranasally or by injection in dosages as known in the art. Danazol, for example, can be administered orally at a daily dose of about 200 mg to about 800 mg for a treatment period of 3-6 months, occasionally extended to 9 months.

In some embodiments, pharmaceutical compositions and delivery systems can include intravaginal administration of androgens such as gestrinone and danazol. For example, gestrinone can be administered by a vaginal route to women with endometriosis so as to reduce dyspareunia and dysmenorrhea with lower side effects such as seborrhea, acne and weight gain as compared to oral administration. Intravaginal administration can include utilization of a vaginal ring or vaginal suppositories as known in the art.

Hormonal therapies can be formulated for administration as a gel, cream, powder, tablet, suppository, capsule, liquid, suspension, dispersion, ointment, foam, etc. formulation and can include additives as are generally known in the art in association with the active agents for the administration route of choice. Additives can include, by way of example and without limitation, emulsifiers, wetness agents, polymeric carriers (e.g., biodegradable polymeric earners), sustained release earners (hyaluronic acid, alginates, carboxymethyl cellulose, hydroxyethyl cellulose, etc.), salts, excipients, dispersions, buffers, and so forth. Preparations for hormonal therapy as may be utilized in treatment of endometriosis have been described, for example, in U.S. Pat. No. 4,997,653 to Igarashi, U.S. Pat. No. 5,993,856 to Ragavan & DiPiano, and U.S. Patent Application Publication No. 2003/0180366 of Kirschner et al., all of which are incorporated herein by reference.

Treatment can also include surgery in those cases in which further examination or development following determination of dysregulation of leukocyte microRNAs includes the discovery of lesions, cysts, adhesions, and so forth that may be present in endometriosis. The goal of surgical treatment is to excise or coagulate all visible endometriotic peritoneal lesions, endometriotic ovarian cysts, deep rectovaginal endometriosis and associated adhesions, and to restore normal anatomy. Laparoscopy can be used in some cases, which can decrease cost, morbidity, and the risk of adhesions postoperatively.

Endometriosis lesions can be removed during laparoscopy by excision, coagulation or vaporization by laser (carbon dioxide laser, potassium-titanyl-phosphate laser or argon laser). In one embodiment, laparoscopic uterine nerve ablation (LUNA) can be utilized. Superficial ovarian lesions can be coagulated or vaporized in one embodiment. Small ovarian endometriomata (e.g., less than about 3 cm diameter) can be aspirated, irrigated, and inspected for intracystic lesions. The interior wall can be coagulated or vaporized to destroy the mucosal lining. Larger ovarian endometriomata (e.g., greater than about >3 cm) can be removed completely). Ovarian cystectomy can also be a treatment option in some embodiments.

Radical procedures such as oophorectomy or total hysterectomy can also be considered, but generally only in severe cases.

Through incorporation of the disclosed diagnostic approaches in treatment of endometriosis, earlier detection and diagnosis of the disease can be possible, which can provide a route to more successful use of less invasive treatment options, such as treatment by use of analgesics and/or hormone therapy, and avoidance of more invasive treatments, such as surgical approaches.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A method for diagnosing and/or treating endometriosis in a subject comprising:

obtaining a peripheral blood sample from a subject;
isolating peripheral blood mononuclear cells from the peripheral blood sample;
purifying a total RNA sample from the peripheral blood mononuclear cells;
analyzing the total RNA sample from the subject to determine a quantity of each leukocyte microRNA of a set of leukocyte microRNAs present in the total RNA sample, wherein the set of leukocyte microRNAs comprises microRNA-1246, microRNA-1225-5p, microRNA-223, microRNA-451, microRNA-572, microRNA-143, microRNA-505, microRNA-155, microRNA-1281, microRNA-93, microRNA-181a-2, microRNA-181a, microRNA-342-5p, microRNA-21, microRNA-339-3p, microRNA-150, microRNA-17, microRNA-181b, microRNA-501-3p, microRNA-27a, microRNA-23a, microRNA-99b, microRNA-342-3p, let-7e, microRNA-769-5p, microRNA-320c, microRNA-1280, microRNA-766, and microRNA-339-5p;
comparing the quantity of each of the leukocyte microRNAs of the set to control quantities of each of the leukocyte microRNAs;
determining based upon the comparison that each of microRNA-1246, microRNA-1225-5p, microRNA-223, microRNA-451, microRNA-572, and microRNA-143, is overexpressed in the total RNA sample by a factor of about 3 or greater;
determining based upon the comparison that each of microRNA-505, microRNA-155, microRNA-1281, microRNA-93, microRNA-181a-2, microRNA-181a, microRNA-342-5p, microRNA-21, microRNA-339-3p, microRNA-150, microRNA-17, microRNA-181b, microRNA-501-3p, microRNA-27a, microRNA-23a, microRNA-99b, microRNA-342-3p, let-7e, microRNA-769-5p, microRNA-320c, microRNA-1280, microRNA-766, and microRNA-339-5p, is underexpressed in the total RNA sample by a factor of about 3 or greater; and
diagnosing the subject with endometriosis and/or administering a treatment for the endometriosis to the subject.

2. The method of claim 1, wherein the total RNA sample is analyzed to obtain a quantity of genetic microRNA, primary microRNA, precursor microRNA and/or mature microRNA of each leukocyte microRNA of the set.

3. The method of claim 1, wherein the step of analyzing the total RNA sample comprises a hybridization-based method, a quantitative real-time PCR method, and/or concentrating or isolating the microRNA from the total RNA sample.

4. The method of claim 1, wherein the treatment comprises administration of an analgesic, administration of one or more hormones, or a surgical treatment.

* * * * *